United States Patent [19]

Jore

[11] Patent Number: 5,507,835
[45] Date of Patent: Apr. 16, 1996

[54] MAGNETIC PROSTHETIC SYSTEM

[76] Inventor: Matthew B. Jore, P.O. Box 735, Ronan, Mont. 59864

[21] Appl. No.: 355,598

[22] Filed: Dec. 13, 1994

[51] Int. Cl.$^6$ ............................................. A61F 2/80
[52] U.S. Cl. ...................................... 623/36; 623/33
[58] Field of Search ...................... 623/33, 36, 34, 623/35, 37–38

[56] References Cited

U.S. PATENT DOCUMENTS

| | | |
|---|---|---|
| 3,140,712 | 7/1964 | Hunter . |
| 3,521,302 | 7/1970 | Müller . |
| 4,024,588 | 5/1977 | Janssen et al. . |
| 4,195,367 | 4/1980 | Kraus ............................. 623/33 |
| 4,214,322 | 7/1980 | Kraus ............................. 623/33 |
| 4,332,037 | 6/1982 | Esformes et al. . |
| 4,743,264 | 5/1988 | Sherva-Parker ................. 623/33 |
| 4,781,720 | 11/1988 | Sherva-Parker ................. 623/33 |
| 4,813,961 | 3/1989 | Sostegni . |
| 5,062,855 | 11/1991 | Rincoe . |

FOREIGN PATENT DOCUMENTS 8800814  2/1988  WIPO ............................ 623/15

*Primary Examiner*—David H. Willse
*Assistant Examiner*—Bruce E. Snow
*Attorney, Agent, or Firm*—Richard C. Conover

[57] ABSTRACT

A first embodiment of the present invention includes a magnetic weight bearing prosthetic socket system for coupling a prosthesis to an amputated limb. A pair of magnetic fixtures are used to hold the prosthesis in spaced apart relation with the amputated limb. One of the magnetic fixtures is implanted in the remnant bone and the other magnetic fixture is embedded in the prosthetic socket. The magnetic fixtures are magnetically oriented to oppose one another and are used to transfer loads associated with typical weight-bearing surfaces through the soft tissue covering the remnant bone without having the magnetic structures physically touch one another.

A second embodiment of the present invention includes repelling magnetic fixtures implanted within opposing bones in an articulating joint to hold the bones apart during relative articulating movement of the bones in the joint.

2 Claims, 7 Drawing Sheets

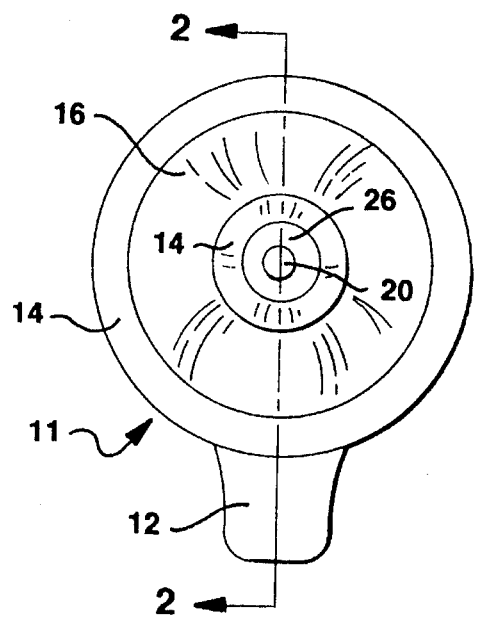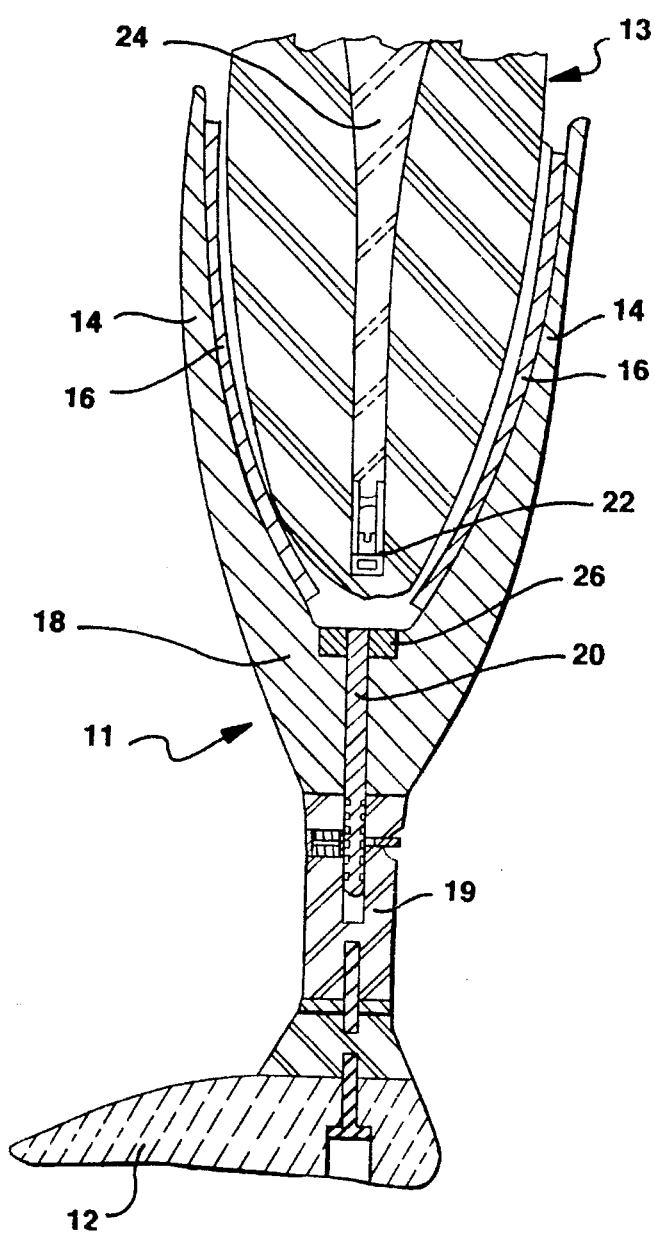
FIG. 1
FIG. 2

MAGNETIC PROSTHETIC SYSTEM

BACKGROUND OF THE INVENTION

A first embodiment of the present invention relates to a magnetic weight-bearing prosthetic socket system for coupling a prosthesis to an artificial limb. In this first embodiment, the system has two opposing magnetic fixtures repelling each other: one implanted at the point of amputation of a bone, and a second incorporated into the prosthesis. In a second embodiment of the present invention opposing magnetic fixtures are implanted into adjacent bone surfaces on either side of an articulating joint. The magnetic fixtures are oriented to repel each other and thus hold the bones apart. In a third embodiment, the magnetic fixtures are positioned in pairs on either side of an articulating joint to reduce lateral movement of the joint.

Artificial joints using magnetism to connect two opposing parts are known. For examples see U.S. Pat. No. 4,332,037 to Esformes et al., Italian patent 514,679 to Rosa, or German patent 320,756 to Heegewaldt. These patents all illustrate the use of the attractive force of magnets to hold a joint in place so that the artificial joint can move in a somewhat normal manner.

It is also true that artificial joints using the repulsive properties of magnets are known. For example, see U.S. Pat. No. 4,024,588 to Janssen et al. However, the illustrated device requires repelling magnets to operate within a cooperatively shaped magnetic socket for the device to work. Soft tissue covering a remnant bone can not be accommodated. The implantation requires that the end of each bone entering the joint be destroyed in order to effect the implantation. The magnets are positioned in a ball and socket relationship.

A need exists for a socket system which can be used to couple a prosthesis to an amputated limb. The socket system should be capable of transferring weight directly between the bone structure and the associated prosthesis without causing pain or discomfort to the person wearing the prosthesis. A first embodiment of this invention has as an object a requirement to transfer weight directly to a remnant bone so that any soft tissue covering the remnant bone will not be rubbed and irritated as the device is being used.

A need also exists for a magnetic system which can be used with an existing but damaged articulating joint to comfortably hold the bones of the joint apart. As the bones rotate in the articulating joint, a repelling force is needed which will keep the bones separated and reduce the friction associated with the rotation of the bones relative to one another. The structure should be capable of being inserted into ends of the bones forming the joint, but at the same time conserve and preserve the preexisting contour of the recipient bones.

A need also exists for a magnetic system which can be used with an existing but damaged articulating joint to comfortably hold the bones of the joint apart and at the same time reduce lateral movement of the joint.

SUMMARY OF INVENTION

A first embodiment of the present invention relates to a magnetic weight bearing prosthetic socket system for coupling a prosthesis to an amputated limb. A pair of magnetic fixtures are used to hold the prosthesis in spaced apart relation with the amputated limb. One of the magnetic fixtures is implanted in the remnant bone and the other magnetic fixture is embedded in the prosthetic socket. The magnetic fixtures are magnetically oriented to oppose one another. The magnetic fixtures for implanting in the remnant bone include a magnetic material vacuously encased inside a material suitable for implantation without having rejection by a body. Suggested materials are, but not limited to, stainless steel, titanium, or medical plastics. The magnetic material, being hermetically sealed inside the implantable material, produces a mechanism for transferring weight from the magnetized implant fixture in the amputated bone to the other magnetized fixture positioned in the prosthesis. The magnetic force of repulsion between these magnets is used to transfer loads associated with typical weight-bearing surfaces through the soft tissue covering the remnant bone without having the magnetic structures physically touch. These repelling magnetic fields also act to dampen shock whenever the prosthesis is forced in a direction against the amputated limb.

Conventionally, the soft tissue covering amputated limbs suffers from the pressure of a prosthetic device transferring body weight to a counteracting bone structure. By using repelling magnetic fixtures wherein magnetic lines of force easily pass through soft tissue, a socket system can be made which transfers weight and shock without pressing a remnant bone against the soft tissue capping the bone.

In a second embodiment of the present invention, repelling magnetic fixtures are implanted within opposing bones in an articulating joint to hold the bones apart. The implanted magnetic fixtures have a cap on the exposed surface that is formed to match a preexisting contour of the bone. By implanting a plurality of magnetic fixtures in one of the joint bones along a direction of rotation, the joint bones are held apart even when the joint is rotated. Optionally, the magnetized fixtures are designed to be orthoscopically adjusted in depth after implantation. This allows the separation between magnets to be adjusted so as to increase or decrease the weight bearing capacity by increasing or decreasing the effects of the magnetic field between the two opposing magnetic fixtures.

A third embodiment of the present invention includes dividing the magnetic fixtures of the second embodiment into pairs with each fixture of each pair being spaced apart from the other fixture of each pair. The spacing distance between the magnetic fixture on one side of the joint is different than the spacing distance on the other side of the joint to help prevent relative lateral movement of the bones comprising the joint.

BRIEF DESCRIPTION OF THE DRAWINGS

In order that the invention may be clearly understood and readily carried into effect, preferred embodiments of the invention will now be described, by way of example only, with reference to the accompanying drawings wherein:

FIG. 1 is a top plan view of a prosthetic socket system of the present invention;

FIG. 2 is a cross-sectional view of the prosthetic socket system and a illustrative prosthesis taken along the line 2—2 in FIG. 1 with an amputated leg inserted in the socket;

FIG. 3 is an enlarged view of the socket portion of the prosthesis shown in FIG. 2 with parts broken away;

DESCRIPTION OF PREFERRED EMBODIMENTS

Figure 4:
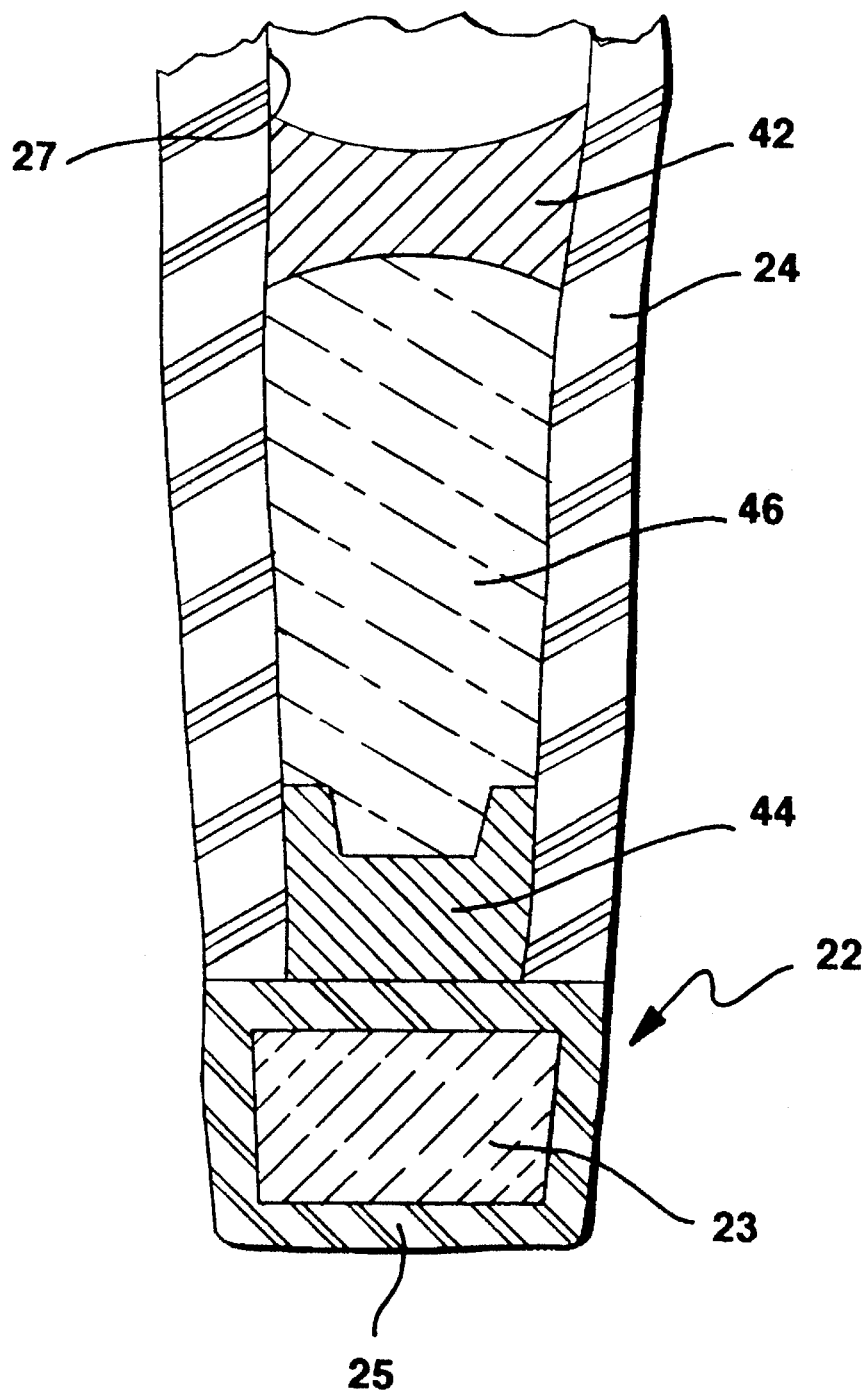
FIG. 4 is an enlarged view of the amputated limb shown in FIG. 2 with parts broken away.
Figure 4:
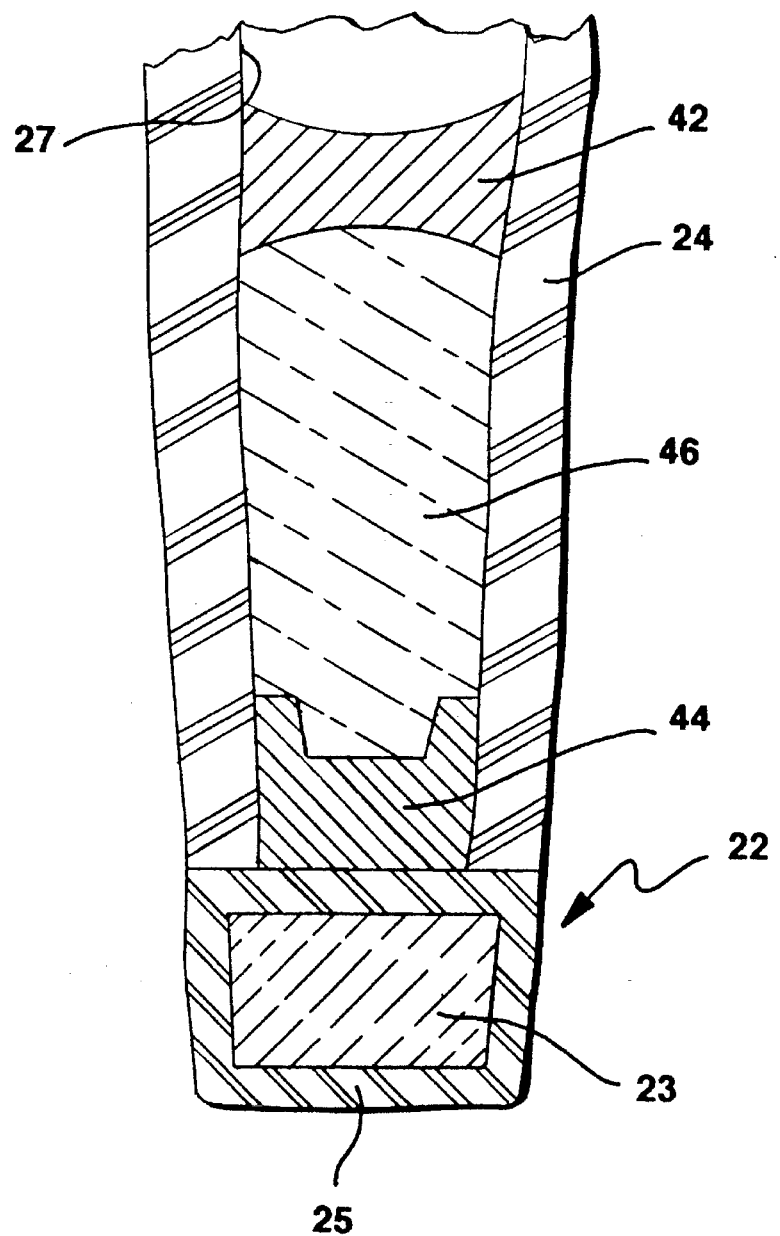

A first preferred embodiment of a magnetic weight-bearing prosthetic socket system is shown in FIG. 1 for coupling a prosthesis 11 to an amputated limb 13. For purposes of illustration only a prosthesis 11 is shown for replacing an amputated ankle. In this illustration, an artificial foot 12 extends from the bottom of prosthesis 11. Prosthesis 11 includes a socket 18 for receiving limb 13 and for this purpose includes a custom-molded sleeve 14 that is a female impression of a surviving portion of limb 13. Socket 18 is shaped to blend into the sleeve 14 as shown in FIG. 2. Sleeve 14, which is resilient, fits over the end of the surviving portion of the limb including remnant bone 24 as shown in FIG. 2. The sleeve 14 may in some instances require additional fastening means (not shown) such as straps, hook-and-loop, or other such devices known in the art to hold the sleeve in place.

Padding 16 is positioned between sleeve 14 and the end of the amputated limb to pad the limb from the prosthesis when the prosthesis is positioned on the amputated limb.

Adjacent the amputated end of remnant bone 24, a first magnetic fixture 22 is fixedly attached. The polarity of magnetic fixture 22 is oriented such that the magnetic lines of force extend generally parallel with the bone through the center of the magnetic fixture 22. Magnetic fixture 22 includes magnet 23 as shown in FIG. 4 hermetically sealed within implantable material 25. Implantable material is material suitable for implantation in a body which material will not be rejected by the body and may include, but is not limited to, materials such as stainless steel, titanium, non-ferrous alloys, and polyethylene.

The present invention requires the implantation of a first magnetic fixture 22 into a living body. As best seen in FIG. 4, bone 24 is resected to have a cavity 27. This cavity 27 receives implantation of first magnetic fixture 22. A support 44 extending from implantable material 25 is positioned in the resected cavity of bone 24. If necessary, an additional extension 46 may be joined to support 44. Bone cement 42, or other fastening means, can be used to hold the implant in place.

A second magnetic fixture 26 is fixedly secured within socket 18 as shown in FIG. 2 and is aligned with its magnetic axis being coaxial with the magnetic axis of magnetic fixture 22 as shown in FIG. 2. Second magnet fixture 26 has its magnetic polarity oriented so as to be repelled by first magnetic fixture 22. When the prosthesis 11 is worn, the magnetic force of repulsion is countered by the opposite force of body weight acting through remnant bone 24. When standing, a point is reached where equilibrium is established between the opposing forces of magnetic repulsion and gravity. Magnetic fixtures 22 and 26 are selected to have sufficient magnetic strength when equilibrium is reached so that the distance between first magnetic fixture 22 and the second magnetic fixture 26 is greater than the thickness of the soft body tissues overlying remnant bone 24.

Sleeve 14 extends from socket 18 to cover the appendage, and by being sized to closely fit over the appendage, prevents second magnetic fixture 26 from moving laterally to escape the repelling magnetic field of first magnetic fixture 22.

As best seen in FIG. 3, a nonferrous rod 20 passes through a bore 28 in second magnetic fixture 26 and extends outwardly and beyond socket 18 into a bone 21 of extension 19 as shown in FIG. 3. At an end of rod 20 extending beyond socket 18, the rod has a plurality of notches 30 for fitting various prosthetic devices to the rod. A latching means 32, which in many prosthetic devices is a spring loaded catch 34, engages a notch 30 cut in rod 20. The extension 19 is connected in a conventional manner to foot 12. In a similar manner various other prosthetic appendages, well known in the art, can be attached to nonferrous rod 20.

In using the first embodiment, a first magnetic fixture 22 is surgically positioned at the remnant end of an amputated bone 24 and attached to the remnant bone. Soft body tissue can then grow back to cover the amputated end of bone 24. Sleeve 14, which is an extension of socket 18, is placed in position to cover the amputated end of remnant bone 24. Socket 18 includes a second magnetic fixture 26 which is magnetically oriented to repel magnetic fixture 22. Nonferrous rod 20, has notches 30 located at the distal end for connecting various prosthetic appendages such as an artificial foot 12. Magnetic fixture 22 acts to repel second magnetic fixture 26 until a distance is reached where the downward acting body weight is supported by an opposite force of magnetic repulsion. The present invention is thus able to transfer weight to remnant bone 24 while avoiding pressure on the soft intervening tissue that covers the remnant bone 24.

Figure 5:
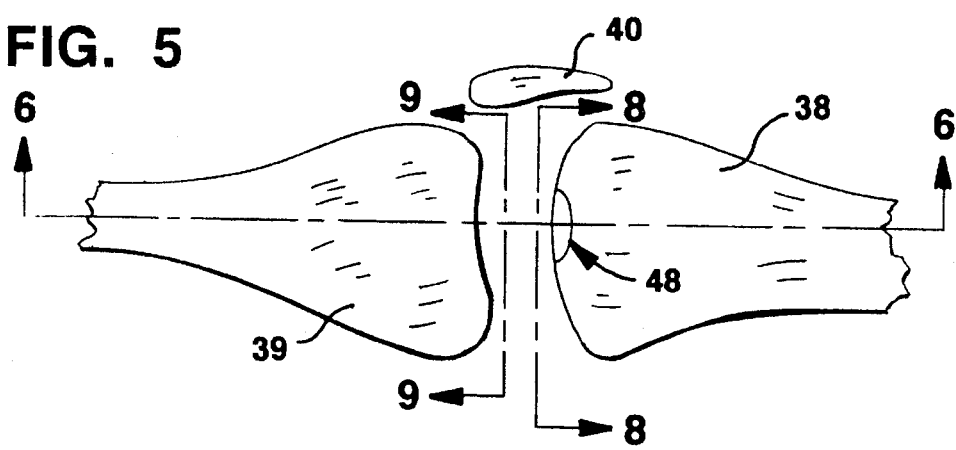
FIG. 5 is an elevational view of a pair of leg bones comprising a knee joint with an embodiment of the present invention installed.

A second embodiment of the present invention is shown in FIGS. 5 through 9 wherein magnetic fixtures are implanted into the opposing articulating surfaces of a joint. It should be recognized that the same system could be used for any of the articulating skeletal joints but for purposes of illustration only, the invention is shown as being used with a knee joint as shown in FIG. 5 with opposing bones 38 and 39 and a knee cap 40.

In this second embodiment, a magnetic fixture 48 is implanted in bone 27 as shown in FIGS. 5, 6, 7 and 8. This magnetic fixture 48, which has a magnet 23 hermetically sealed in implantable material 29, has a magnetic field that is oriented substantially perpendicular to the surface of bone 38. One of the two poles of the magnetic fixture is exposed and positioned adjacent the surface of bone 38. A cap 52 is attached adjacent the exposed end to conform the exposed surface of magnetic fixture 48 to the exterior surface of bone 38. If the external contour of bone 38 is damaged, cap 52 is shaped to fit the contour of bone 38 in a form similar to a preexisting, undamaged bone so that the external contour of bone 38 appears similar to the contour associated with its undamaged state. Additional magnetic fixtures 49, which are similar to magnetic fixtures 48, are implanted in bone 38 along the direction of articulation and are magnetically oriented the same as magnetic fixture 48.

Figure 6:
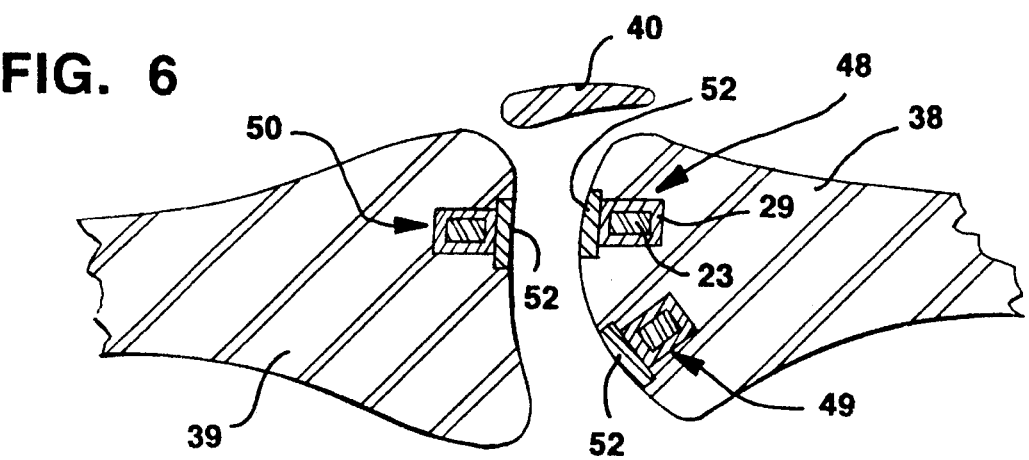
FIG. 6 is a cross sectional view of the knee joint shown in FIG. 5 along the medial line 6—6 in FIG. 5 looking into the paper.
Figure 7:
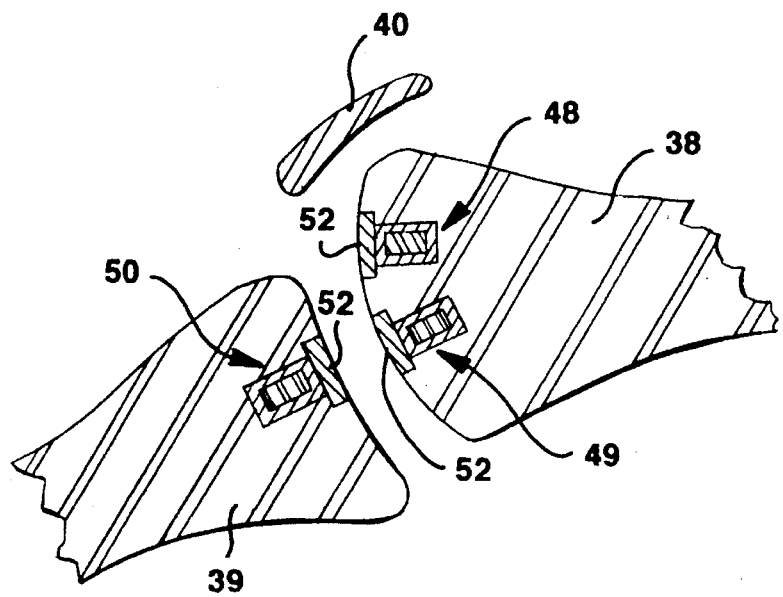
FIG. 7 is the view shown in FIG. 6 with the knee bones positioned in a different articulated position.
Figure 8:
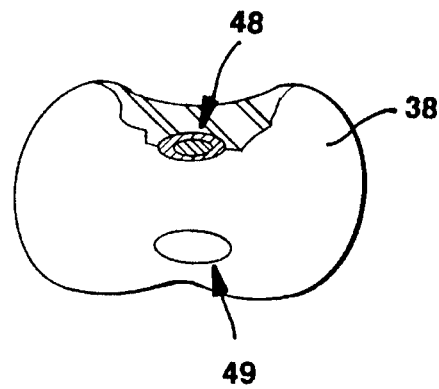
FIG. 8 is a view along the line 8—8 in FIG. 5 with portions broken away.
Figure 9:
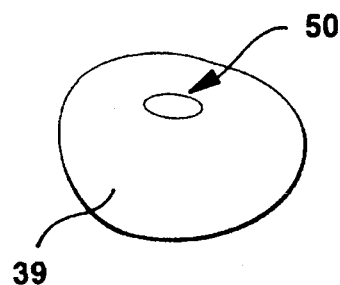
FIG. 9 is a view along the line 9—9 in FIG. 5.
Figure 10:
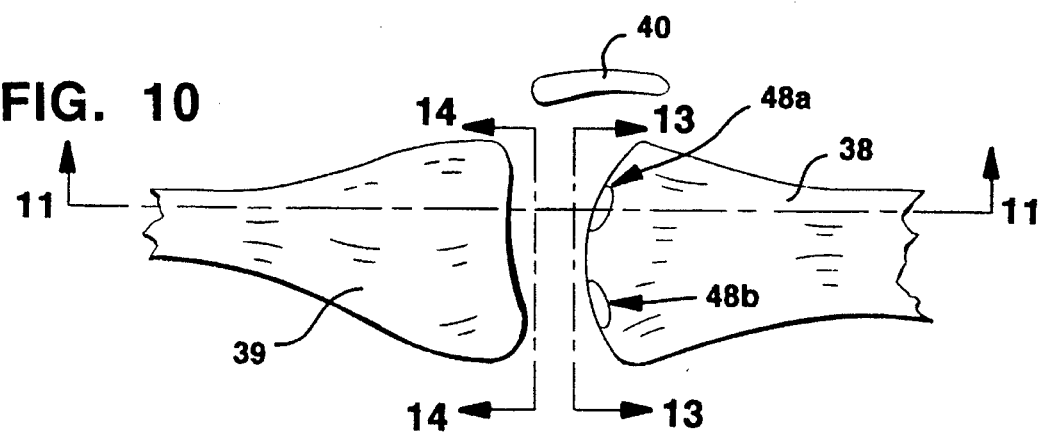
FIG. 10 is an elevational view of a pair of leg bones comprising a knee joint with another embodiment of the present invention installed.

Magnetic fixture 50, which is also similar to magnetic fixture 48, is implanted in the opposite bone 39 of the articulated joint as shown in FIGS. 6, 7 and 9 with a polarity oriented so as to be repelled by magnetic fixtures 48 and 49. As the joint is moved, magnetic fixture 50 is moved away from opposing magnetic fixture 48 but is moved closer to adjacent magnetic fixture 49 as shown in FIG. 7. By using additional magnetic fixtures 49 as needed, the magnetic forces of repulsion can act to keep the two opposing bones separated as the articulating joint is moved throughout its range.

In using the second embodiment, magnetic fixtures 48 and 50 are implanted in opposing bones in an articulating joint so as to use the magnetic force of repulsion to force the opposing bones apart. If the opposing bones can normally move through a considerable arc at the articulating Joint, additional magnetic fixtures 49 are installed on one side of the joint to keep the force of repulsion operating nearly perpendicular to the contoured surfaces of the bone.

In a third embodiment, which is a variation of the second embodiment, magnetic fixtures 48, 49, and 50 can be implanted in bones 38 and 39 so as to help prevent lateral joint movement. As best seen in FIGS. 10 through 14, each of the magnetic fixtures 48, 49 and 50 of the second embodiment are replaced with a spaced apart pair 48a, 48b, 49a, 49b, 50a and 50b to provide additional lateral support in a direction parallel with an axis of rotation. The centers of a pair of magnetic fixtures 48a and 48b on one side of a joint are placed outside the centers of a pair of magnetic fixtures 50a and 50b on the opposite side of the joint. The repelling force between these opposing magnets helps to prevent lateral joint movement when such movement is not desired because the magnetic repulsive force grows considerable stronger as the bones of the joint are moved laterally. The increased repulsive force acts to center an opposing pair of magnetic fixtures.

Figure 11:
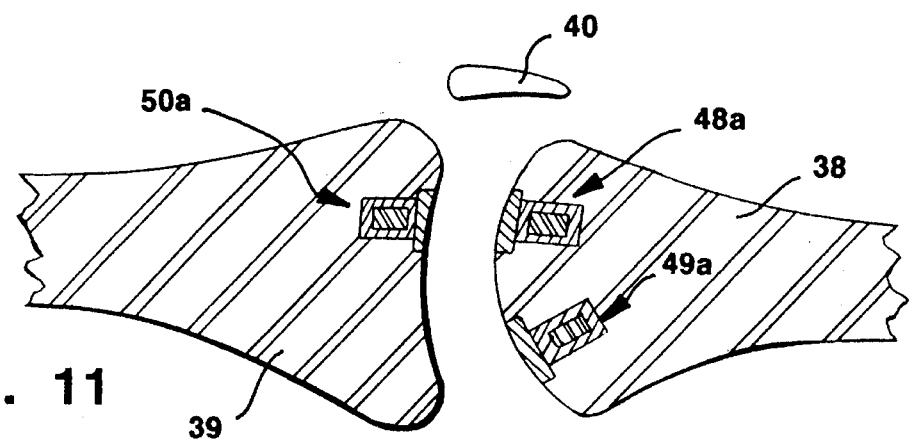
FIG. 11 is a cross sectional view of the knee joint shown in FIG. 10 along the medial line 11—11 in FIG. 10 looking into the paper.
Figure 12:
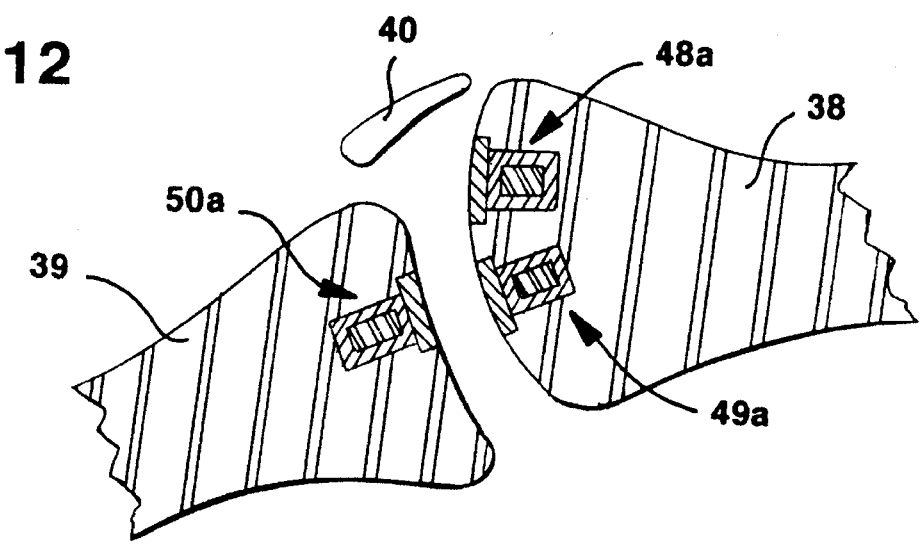
FIG. 12 is the view shown in FIG. 11 with the knee bones positioned in a different articulated position.
Figure 13:
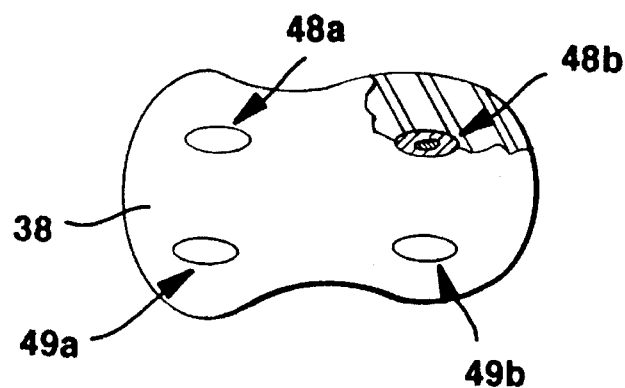
FIG. 13 is a view along the line 13—13 in FIG. 10 with portions broken away.
Figure 14:
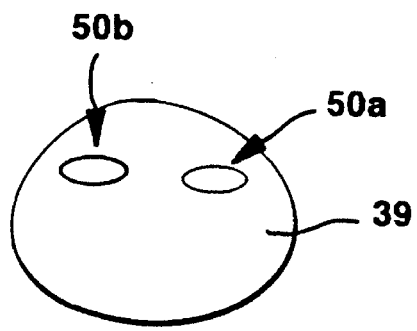
FIG. 14 is a view along the line 14—14 in FIG. 10.

Any additional pairs of magnetic fixtures, such as 49a and 49b as shown in FIG. 11, 12 and 13, also have the same lateral spacing as the other pair of magnetic fixtures 48a and 48b on the same side of the joint.

Figure 15:
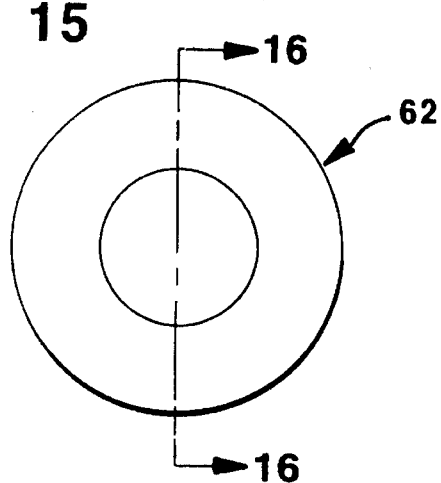
FIG. 15 is an end view of a magnetic fixture holder according to the present invention.
Figure 16:
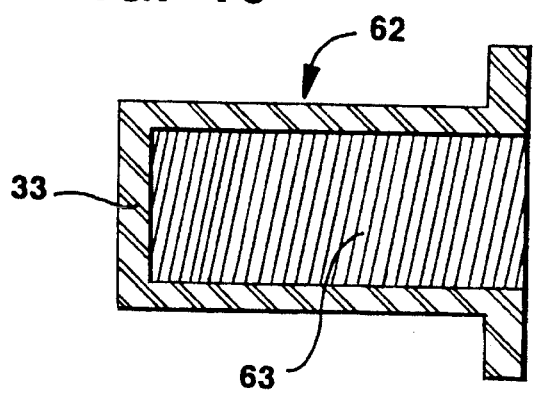
FIG. 16 is a cross sectional view along line 16—16 in FIG. 15.
Figure 17:
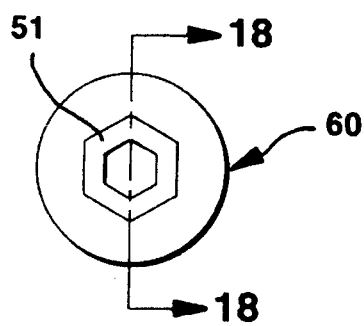
FIG. 17 is an end view of an embodiment of a magnetic fixture according to the present invention.
Figure 18:
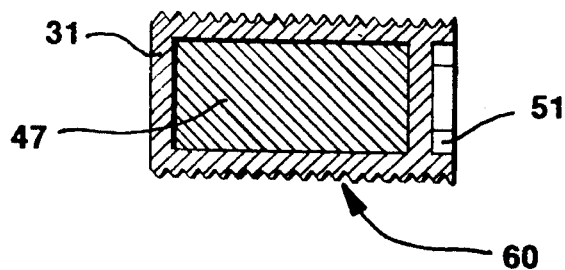
FIG. 18 is a cross sectional view along line 18—18 in FIG. 17.

FIGS. 15 through 18 show magnetically adjustable magnetic fixtures which may be substituted for any or all of the magnetic fixtures shown in FIGS. 5–14. In the adjustable design, magnet 47 is hermetically sealed within an implantable material 31 to form an encased magnetic fixture 60. Encased magnetic fixture 60 is externally threaded as shown in FIG. 18 to be threadably received by a holder 62 as shown in FIGS. 15 and 16. Holder 62 is constructed of implantable material 33 and includes an internally threaded bore 63 to accept encased magnetic fixtures 60. The internal threading of holder 62 is much longer than encased magnetic fixtures 60 so that the encased magnetic fixture can be adjustably positioned in depth within holder 62. The magnetic fixture 60 also includes a tool receiving means 51 located at one end to allow for a tool to be used to screw magnetic fixture 60 into holder 62. The further magnetic fixture 60 is screwed into holder 62, the weaker the magnetic field exiting holder 62.

While the fundamental novel features of the invention have been shown and described, it should be understood that various substitutions, modifications and variations may be made by those skilled in the art without departing from the spirit or scope of the invention. Accordingly, all such modifications or variations are included in the scope of the invention as defined by the following claims:

I claim:

1. A magnetic weight bearing prosthetic socket system for coupling a prosthesis to an amputated limb having an amputated bone comprising:

a first magnetic fixture having distal and proximal ends, said distal end having a magnet, said proximal end fixedly securable to an amputated end of the bone;

an amputated limb socket for attaching a prosthesis having a sleeve for removeably receiving the amputated limb;

a second magnetic fixture fixedly secured to the socket and positioned to have its magnetic axis coaxial with the magnetic axis of the first magnetic fixture; and the second magnetic fixture being oriented so that the magnetic fields of the first magnetic fixture and the second magnetic fixture repel each other.

2. The system according to claim 1 wherein the first magnetic fixture is encased in an implantable material.

* * * * *